(12) United States Patent
Umeda et al.

(10) Patent No.: US 8,346,340 B2
(45) Date of Patent: Jan. 1, 2013

(54) MAGNETIC RESONANCE IMAGING APPARATUS AND MAGNETIC RESONANCE IMAGING METHOD

(75) Inventors: Masaaki Umeda, Sakura (JP); Toshio Fukuta, Otawara (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 1042 days.

(21) Appl. No.: 12/238,486

(22) Filed: Sep. 26, 2008

(65) Prior Publication Data

US 2009/0124885 A1    May 14, 2009

(30) Foreign Application Priority Data

Sep. 27, 2007 (JP) ................... 2007-252401

(51) Int. Cl.
*A61B 5/05* (2006.01)
(52) U.S. Cl. .................... 600/410; 600/407; 600/417
(58) Field of Classification Search .......... 600/407, 600/410, 417
See application file for complete search history.

(56) References Cited

U.S. PATENT DOCUMENTS

| 6,369,568 | B1 | 4/2002 | Ma et al. |
| 7,323,873 | B2 | 1/2008 | Yamazaki |
| 2008/0009701 | A1* | 1/2008 | Avram et al. ............... 600/410 |

OTHER PUBLICATIONS

James G. Pipe, "Motion Correction With Propeller MRI: Application to Head Motion and Free-Breathing Cardiac Imaging," Magnetic Resonance in Medicine, 42, pp. 963-969, 1999 Wiley-Liss, Inc.

* cited by examiner

*Primary Examiner* — Brian L. Casler
*Assistant Examiner* — Joel Lamprecht
(74) *Attorney, Agent, or Firm* — Nixon & Vanderhye PC

(57) ABSTRACT

A apparatus includes a collection unit which collects a magnetic resonance signal, a unit which controls the collection unit in such a manner that pre-scan is executed in regard to pre-scan slices determined as some of main scan slices, a calculation unit which calculates correction amounts based on data concerning the pre-scan slices obtained by the pre-scan, an estimation unit which estimates a correction amount concerning each slice other the pre-scan slices in the main scan slices based on the correction amounts, and a unit which controls the collection unit in such a manner that each of the main scan slices is scanned while involving correction of each slice that is the pre-scan target with the correction amount thereof calculated by the calculation unit and while involving correction of each slice that is not the pre-scan target with the correction amount thereof estimated by the estimation unit.

9 Claims, 4 Drawing Sheets

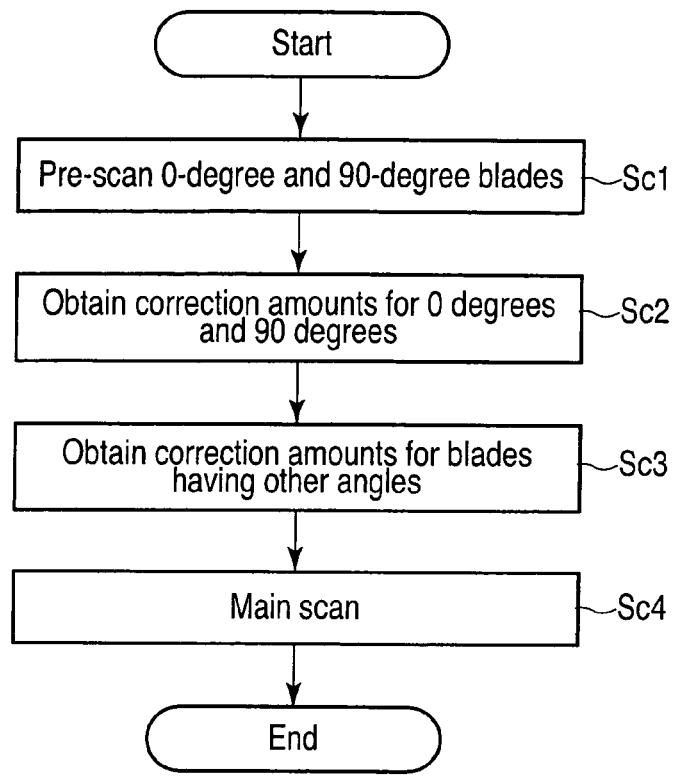
F I G. 6
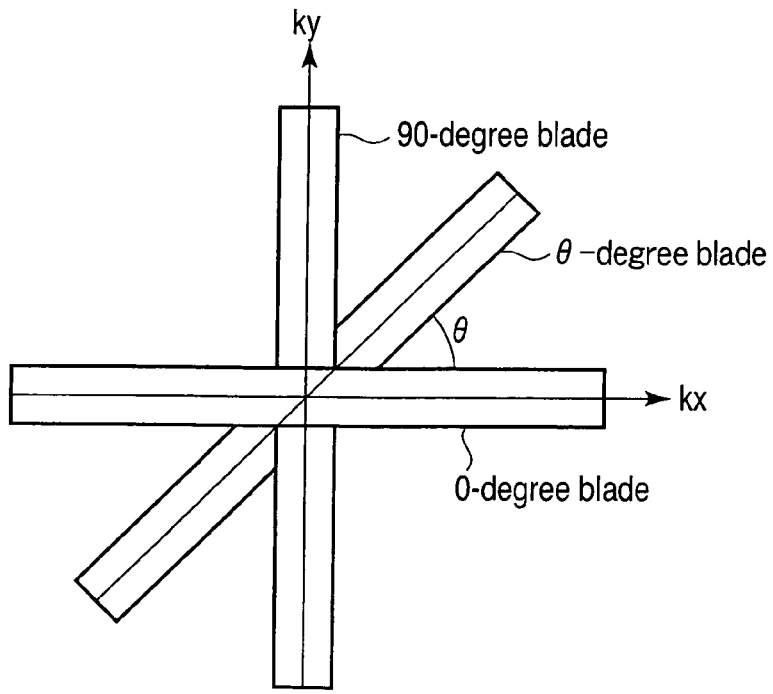
F I G. 7

MAGNETIC RESONANCE IMAGING APPARATUS AND MAGNETIC RESONANCE IMAGING METHOD

CROSS-REFERENCE TO RELATED APPLICATIONS

This application is based upon and claims the benefit of priority from prior Japanese Patent Application No. 2007-252401, filed Sep. 27, 2007, the entire contents of which are incorporated herein by reference.

BACKGROUND OF THE INVENTION

1. Field of the Invention

The present invention relates to a magnetic resonance imaging apparatus and a magnetic resonance imaging method that collect magnetic resonance signals concerning a subject in a fast spin echo (FSE) sequence or a fast asymmetric spin echo (FASE) sequence.

2. Description of the Related Art

In this type of magnetic resonance imaging, a phase shift of spin echoes is detected based on pre-scan. In main scan, the detected phase shift is corrected.

For example, according to a technology disclosed in U.S. Pat. No. 6,369,568, spin echoes which are not subjected to phase encoding (PE) are collected, and zeroth order and first order phase differences of a first echo and a second echo are measured. Further, the zeroth order phase difference is mainly corrected by adjusting a phase of an RF at the time of main scan, and the first order phase difference is corrected by adding a correction pulse to a gradient magnetic field pulse in a readout direction at the time of main scan.

It is to be noted that a correction amount for a phase shift varies depending on each slice when the main scan is performed with respect to a plurality of slices. Furthermore, when a method of filling a k-space while rotating a blade (see, e.g., Magnetic Resonance in Medicine Vol 42, 963-969, 1999) is applied to the main scan, a correction amount for a phase shift varies depending on each blade.

Therefore, pre-scan is carried out with respect to all slices or blades as targets of the main scan.

As explained above, since the pre-scan is carried out with respect to all slices or blades as targets of the main scan in the conventional technology, a time required for the pre-scan is long depending on imaging conditions.

BRIEF SUMMARY OF THE INVENTION

Due to the above-explained circumstances, it has been demanded to enable a reduction in time required for the pre-scan while correcting all slices or blades as targets of the main scan to enable taking an image with less image quality degradation.

According to a first aspect of the present invention, there is provided a magnetic resonance imaging apparatus comprising: a collection unit which collects a magnetic resonance signal concerning a subject in a fast spin echo sequence or a fast asymmetric spin echo sequence; a pre-scan control unit which controls the collection unit in such a manner that pre-scan is executed in regard to a plurality of slices determined as some of a plurality of slices that are main scan targets; a calculation unit which calculates at least one of correction amounts for a gradient magnetic field in a readout direction and a phase of a radio-frequency pulse based on data concerning a plurality of slices obtained by the pre-scan; an estimation unit which estimates a correction amount concerning each slice other the plurality of pre-scanned slices in the plurality of slices that are the main scan targets based on a plurality of correction amounts calculated by the calculation unit; and a main scan control unit which controls the collection unit in such a manner that each of the plurality of slices as the main scan targets is scanned while involving correction of each slice that is the pre-scan target with the correction amount thereof calculated by the calculation unit and while involving correction of each slice that is not the pre-scan target with the correction amount thereof estimated by the estimation unit.

According to a second aspect of the present invention, there is provided a magnetic resonance imaging apparatus comprising: a collection unit which collects a magnetic resonance signal concerning a subject in accordance with each of blades including a plurality of k-space trajectory parallel to each other and having different inclinations in the k-space in one of a fast spin echo sequence and a fast asymmetric spin echo sequence; pre-scan control unit which controls the collection unit in such a manner that a plurality of blades determined as some of a plurality of blades that are main scan targets are pre-scanned; a calculation unit which calculates a calculation amount for at least one of a gradient magnetic field in a readout direction and a phase of a radio-frequency pulse based on data concerning a plurality of blades obtained by the pre-scan; an estimation unit which estimates a correction amount in regard to each blade other than the pre-scan target blades in the plurality of main scan target blades based on a plurality of correction amounts calculated by the calculation unit; and a main scan control unit which controls the collection unit in such a manner that each of the plurality of blades as the main scan targets is scanned while involving correction for each of the blades that are the pre-scan targets with a correction amount thereof calculated by the calculation unit or while involving correction for each of the blades that are not the pre-scan targets with a correction amount thereof estimated by the estimation unit.

According to a third aspect of the present invention, there is provided a magnetic resonance imaging method in a magnetic resonance imaging apparatus including a collection unit which collects a magnetic resonance signal concerning a subject in a fast spin echo sequence or a fast asymmetric spin echo sequence, comprising: controlling the collection unit in such a manner that a plurality of slices determined as some of a plurality of slices that are main scan targets are pre-scanned; calculating a correction amount for at least one of a gradient magnetic field in a readout direction or a phase of a radio-frequency pulse based on data concerning a plurality of slices obtained by the pre-scan; estimating a correction amount concerning each slice other than the plurality of pre-scanned slices in the plurality of slices that are the main scan targets based on the plurality of calculated correction amounts; and controlling the collection unit in such a manner that each of the plurality of slices that are the main scan targets is scanned while involving correction for each of the slices as the pre-scan targets with the calculated correction amount thereof or while involving correction of each of the slices that are not the pre-scan targets with the estimated correction amount thereof.

According to a fourth aspect of the present invention, there is provided a magnetic resonance imaging method in a magnetic resonance imaging apparatus including a collection unit which collects a magnetic resonance signal concerning a subject in accordance with each of blades including a plurality of k-space trajectory parallel to each other and having different inclinations in the k-space in one of a fast spin echo sequence or a fast asymmetric spin echo sequence, comprising: controlling the collection unit in such a manner that a plurality of blades determined as some of a plurality of blades that are main scan targets are pre-scanned; calculating a correction amount for at least one of a gradient magnetic field in a readout direction and a phase of a radio-frequency pulse based on data concerning a plurality of blades obtained by the pre-scan; estimating a correction amount of each blade other than the pre-scan target blades in the plurality of main scan target blades based on the plurality of calculated correction amounts; and controlling the collection unit in such a manner that each of the plurality of blades that are the main scan targets is scanned while involving correction of each of the blades that are the pre-scan targets with the calculated correction amount thereof or while involving correction of each of the blades that are not the pre-scan targets with the estimated correction amount thereof.

Additional objects and advantages of the exemplary embodiments will be set forth in the description which follows, and in part will be obvious from the description, or may be learned by practice. The objects and advantages of the exemplary embodiments may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate exemplary embodiments of the invention, and together with the general description given above and the detailed description of the embodiments given below, serve to explain principles of the exemplary embodiments.

FIG. 6 is a flowchart showing an example of a processing procedure of the main controller in FIG. 1 according to the third embodiment; and FIG. 7 is a view showing a relationship between a blade as a target of pre-scan and other blades.

DETAILED DESCRIPTION OF EXEMPLARY EMBODIMENTS

First to third embodiments according to the present invention will now be explained hereinafter with reference to the accompanying drawings.

Figure 1:
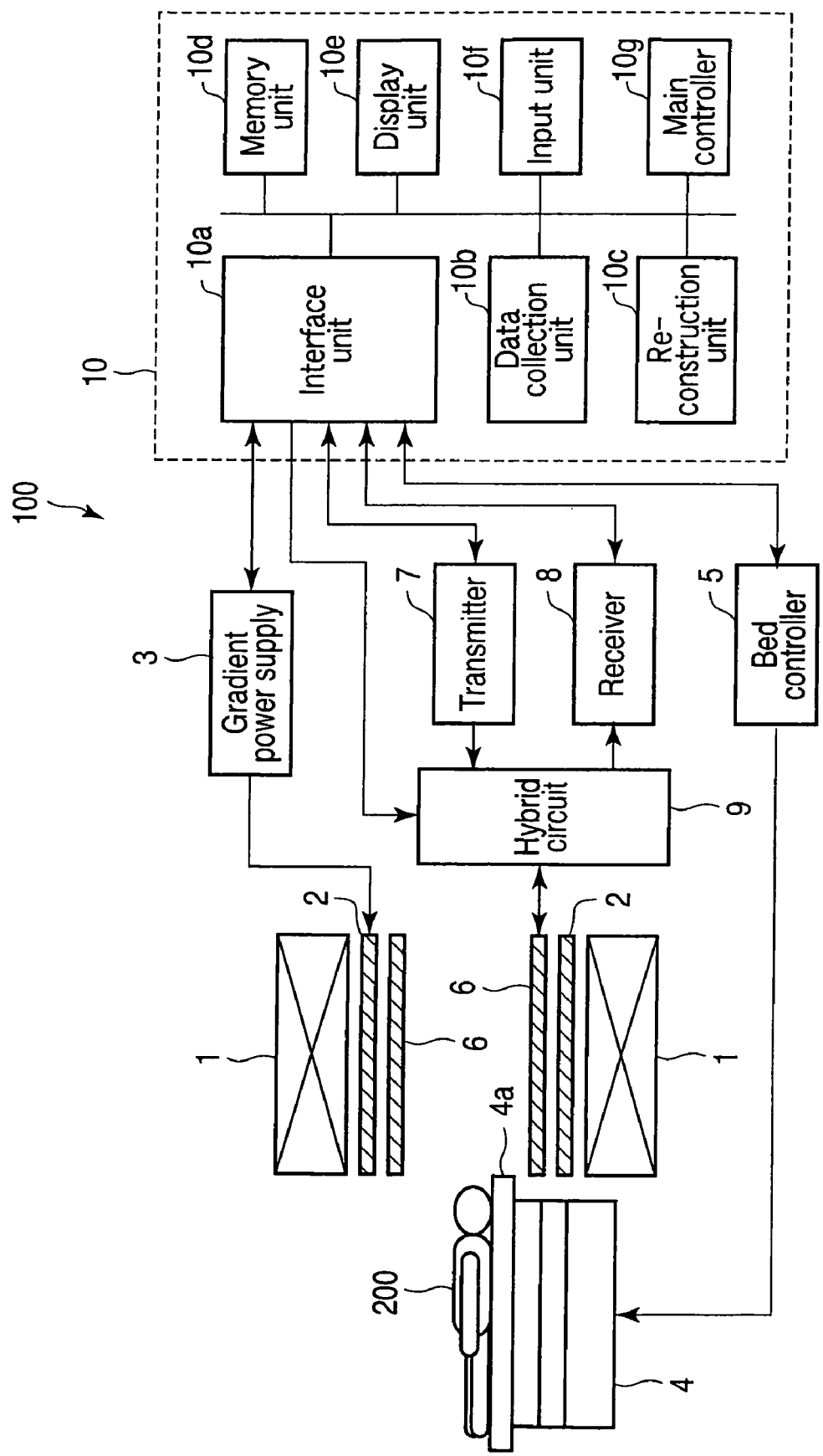
FIG. 1 is a view showing a structure of a magnetic resonance imaging apparatus according to first to third embodiments of the present invention.

FIG. 1 is a view showing a structure of a magnetic resonance imaging apparatus (which will be referred to as an MRI apparatus hereinafter) 100 according to the first to third embodiments. This MRI apparatus 100 includes a static field magnet 1, a gradient coil 2, a gradient power supply 3, a bed 4, a bed controller 5, an RF coil 6, a transmitter 7, a receiver 8, a hybrid circuit 9, and a computer system 10.

The static field magnet 1 has a hollow cylindrical shape and generates a uniform static magnetic field within its inside space. As this static field magnet 1 use is made of a permanent magnet, a superconducting magnet, or the like.

The gradient coil 2 is formed in the shape of a hollow cylinder and placed inside the static field magnet 1. The gradient coil 2 is a combination of three coils each corresponding to a respective one of the three mutually orthogonal X, Y, and Z axes. When the three coils are individually supplied with a current from the gradient power supply 3, the gradient coil 2 generates gradient magnetic fields each of which has its strength varied along a corresponding one of the X, Y, and Z axes. It is to be noted that the Z-axis direction coincides with the direction of the static magnetic field. The gradient magnetic fields along the X-, Y-, and Z-axes are associated with, e.g., a slice selecting gradient magnetic field Gs, a phase encoding gradient magnetic field Ge, and a readout gradient magnetic field Gr, respectively. The slice selecting gradient magnetic field Gs is used to arbitrarily determine an imaging slice. The phase encoding gradient magnetic field Ge is used to change a phase of magnetic resonance signals according to a spatial location. The readout gradient magnetic field Gr is used to change a frequency of the magnetic resonance signals according to a spatial location.

A subject 200 is laid down on a top board 4a of the bed 4 and moved into a cavity of the gradient coil 2 in this state. The top board 4a is driven by the bed controller 5 to move lengthwise and up and down. Usually, the bed 4 is installed so that its longitudinal axis is parallel to the central axis of the static field magnet 1.

The RF coil 6 is placed inside the gradient coil 2. The RF coil 6 generates a radio-frequency magnetic field in response to application thereto of a radio-frequency (RF) pulse from the transmitter 7. The RF coil 6 detects magnetic resonance signals from the subject 200. The magnetic resonance signal output from the RF coil 6 is inputs to the receiver 8.

The transmitter 7 transmits RF pulses corresponding to a Larmor frequency.

The receiver 8 has a preamplifier, a phase detector, and an analog/digital converter. The preamplifier amplifies a magnetic resonance signal output from the hybrid circuit 9. The phase detector detects a phase of a magnetic resonance signal output from the preamplifier. The analog/digital converter converts a signal output from the phase detector into a digital signal.

The hybrid circuit 9 supplies a radio-frequency pulse fed from the transmitter 7 to the RF coil 6 in a transmission period. The hybrid circuit 9 supplies a signal output from the RF coil 6 to the receiver 8 in a reception period. The transmission period and the reception period are indicated by the computer system 10. Additionally, the hybrid circuit 9 can be connected with a local RF coil. When the local RF coil is connected, the hybrid circuit 9 supplies a radio-frequency pulse to one of the RF coil and the local RF coil, and supplies a signal output from one of the RF coil and the local RF coil to the receiver 8. The computer system 10 instructs to select one of the RF coil and the local RF coil.

The computer system 10 has an interface unit 10a, a data collection unit 10b, a reconstruction unit 10c, a memory unit 10d, a display unit 10e, an input unit 10f, and a main controller 10g.

The interface unit 10a is connected to the gradient power supply 3, the bed controller 5, the transmitter 7, the receiver 8, and the hybrid circuit 9. The interface unit 10a inputs/outputs signals transmitted/received between these selected respective units and the computer system 10.

The data collection unit 10b collects digital signals output from the receiver 8. The data collection unit 10b stores the collected digital signals as magnetic resonance signal data in the memory unit 10d.

The reconstruction unit 10c performs postprocessing, i.e., reconstruction such as Fourier transforms, on the magnetic resonance signal data stored in the memory unit 10d to obtain spectrum data of desired nuclear spins within the subject 200 or image data.

The memory unit 10d stores magnetic resonance signal data and spectrum data or image data for each subject.

The display unit 10e displays spectrum data or image data and a variety of information under control of the main controller 10g. As the display unit 10e, there is available a display device such as a liquid crystal display.

The input unit 10f receives a variety of commands or information inputs from an operator. As the input unit 10f, there is available a pointing device such as a mouse or a trackball, a selection device such as a mode changeover switch, or an input device such as a keyboard in accordance with the occasion.

The main controller 10g is equipped with a CPU, a memory, etc., and collectively controls the MRI apparatus 100.

Thus, in this MRI apparatus 100, the gradient power supply 3, the transmitter 7, the receiver 8, the hybrid circuit 9, and the data collection unit 10b function as a collection unit.

This MRI apparatus 100 carries out main scan based on an FSE sequence. In the main scan, imaging data required to fill a k-space is collected. In the FSE sequence, a plurality of flop pulses are given after the end of one flip pulse to generate a spin echo train. At this time, spin echoes included in the spin echo train are associated with respective different lines in the k-space by applying phase encoding with different intensities to the respective spin echoes. As explained above, in the FSE sequence, a plurality of different views are collected by a single excitation.

In the FSE sequence, sensitivity unevenness or a reduction in signal-to-noise ratio (SNR) may occur because of a deviation from Carr-Purcell-Meiboom-Gill (CPMG) conditions due to an eddy current. Thus, the main controller 10g executes pre-scan prior to the main scan. In the pre-scan, data that is used to determine a phase correction amount of RF pulses in the main scan is collected. This pre-scan may be executed to collect data for the above-explained purpose alone, or it may be also used as existing scan that is adopted to collect data for determining a correction amount of spoiler pulses or flow compensation pulses.

The first to third embodiments are mainly characterized in an operation in the pre-scan.

Characteristics of each embodiment will now be specifically explained hereinafter.

First Embodiment

In the first embodiment, the main controller log serves as a unit that realizes the following several functions besides a unit that realizes functions generally provided in the MRI apparatus. One of the functions is controlling the gradient power supply 3, the transmitter 7, the receiver 8, the hybrid circuit 9, the data collection unit 10b, and others in such a manner that the pre-scan is executed with respect to each slice per repetition time. It is to be noted that, as slices that are targets of the pre-scan (which will be referred to as pre-scan slices hereinafter), a plurality of slices as some of a plurality of slices as targets of the main scan (which will be referred to as main scan slices hereinafter) are allocated in advance. One of the functions is calculating a correction amount for each of the main scan slices as the pre-scan slices based on a result of the pre-scan with respect to each slice. One of the functions is estimating a correction amount concerning each slice other than the pre-scan slices in the main scan slices based on each of the plurality of calculated correction amounts. One of the functions is controlling the gradient power supply 3, the transmitter 7, the receiver 8, the hybrid circuit 9, the data collection unit 10b, and others in such a manner that each of the main scan slices is scanned in a sequential mode while involving correction with the correction amount for each slice.

An operation of the MRI apparatus 100 in the first embodiment will now be explained.

In the first embodiment, the main scan is executed in the sequential mode. In the sequential mode, data of N slices (the main scan slices) in a single slab is collected in accordance with each slice per repetition time TR. In the pre-scan, data concerning a plurality of slices as some of the main scan slices alone is collected in accordance with each slice per reception time TR.

Figure 2:
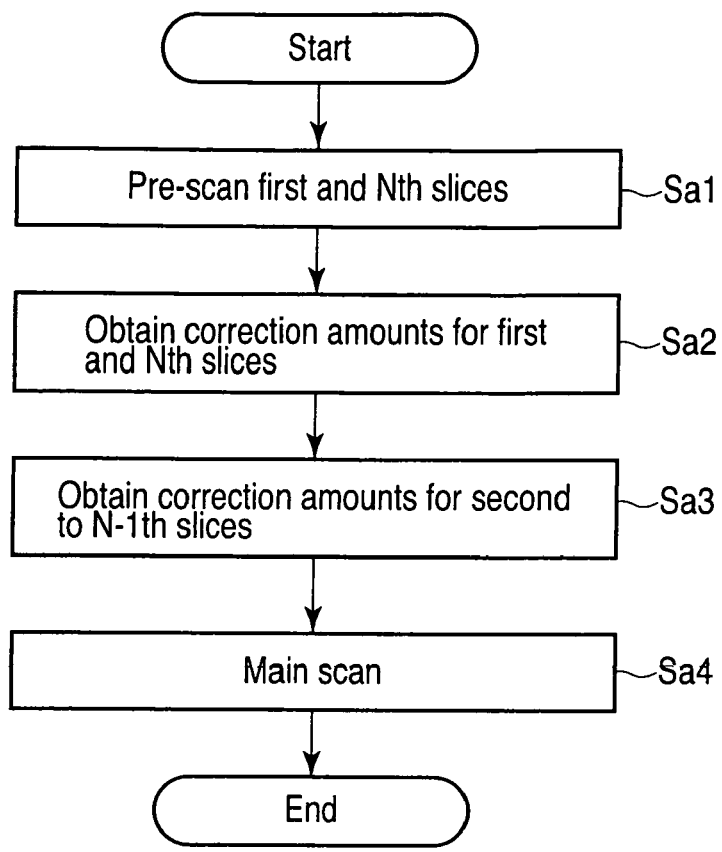
FIG. 2 is a flowchart showing an example of a processing procedure of a main controller in FIG. 1 according to the first embodiment.

FIG. 2 is a flowchart showing an example of a processing procedure of the main controller 10g in the first embodiment.

At step Sa1, the main controller 10g controls the gradient power supply 3, the transmitter 7, the receiver 8, the hybrid circuit 9, and the data collection unit 10b in such a manner that data concerning first and Nth slices alone in the main scan slices is collected in accordance with each slice per repetition time TR. As a result, the pre-scan targeting the first and Nth slices alone in the main scan slices is executed.

At step Sa2, the main controller 10g obtains each of correction amounts concerning the first and Nth slices based on the data collected by the pre-scan. A known technique can be used for this operation. For example, the phase correction amount of an RF pulse used for correcting the zeroth order phase difference is obtained as an amount that is ½ of a phase difference measured at peak positions of first and second echoes. Alternatively, the phase correction amount is obtained as an amount that is ½ of a phase difference of first and second echoes obtained after Fourier transformation.

Figure 3:
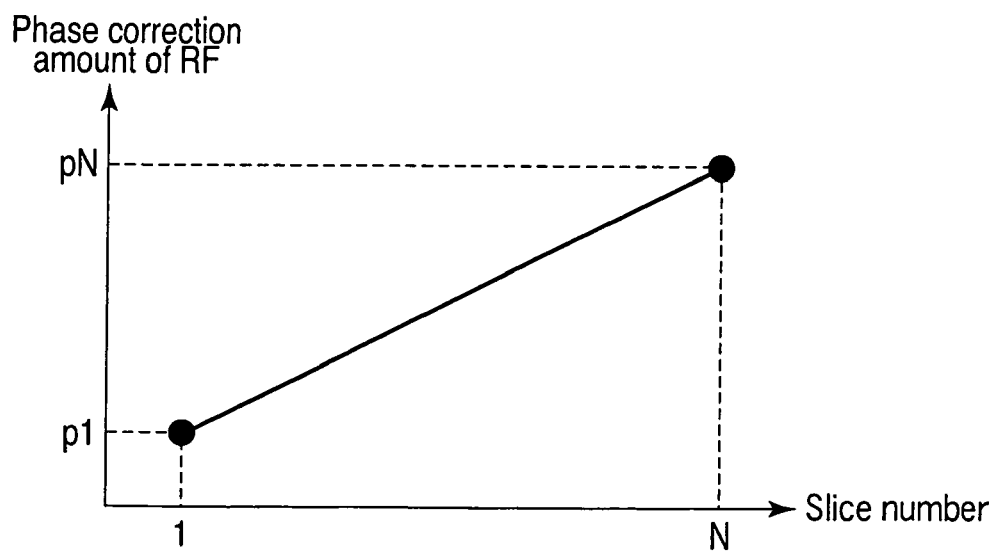
FIG. 3 is a view showing a concept of processing for obtaining a correction amount concerning a slice that is not a target of pre-scan.

At step Sa3, the main controller 10g obtains p correction amounts concerning second to N−1th slices that are not pre-scan targets in the main scan slices based on the correction amounts acquired in regard to the first and the Nth slices as the pre-scan slices. For example, in regard to a correction amount about the readout direction, an average value of the correction amounts acquired in relation to the first and Nth slices is determined as a correction amount common to all slices. A correction amount for a phase of a 180-degree pulse is obtained by linear interpolation based on the correction amounts acquired in relation to the first and Nth slices. That is, for example, as shown in FIG. 3, assuming that the correction amount acquired in relation to the first slice is p1 and the correction amount acquired in relation to the Nth slice is pN, a correction amount a(j) concerning a jth slice is represented by a straight line connecting p1 with pN. That is, the correction amount a(j) is calculated by the following Expression (1).

$$a(j)=p1+(pN-p1)/(N-1)\times(j-1) \qquad (1)$$

At step Sa4, the main controller 10g controls the gradient power supply 3, the transmitter 7, the receiver 8, the hybrid circuit 9, and the data collection unit 10b to execute the main scan. At this time, a 180-degree pulse obtained by correcting a phase based on the correction amounts acquired at step Sa2 is used in the main scan concerning the first and Nth P slices, and a 180-degree pulse obtained by correcting a phase based on the correction amounts acquired at step Sa3 is used in the main scan concerning the second to N−1th slices.

Thus, according to this embodiment, assuming that the number of the pre-scan slices is M, a pre-scan time is reduced to M/N as compared with a case where N main scan slices are all subjected to the pre-scan. Specifically, for example, the main controller 10g controls the gradient power supply 3, the transmitter 7, the receiver 8, the hybrid circuit 9, and the data collection unit 10b in such a manner that to collect data of slices at both ends in a slab alone. In this case, the pre-scan time is reduced to 2/N.

Figure 4:
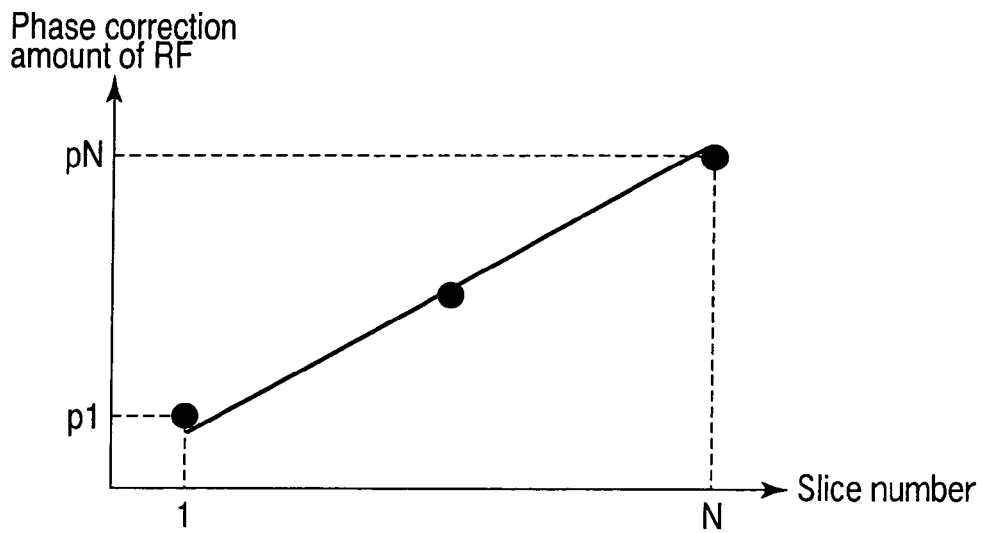
FIG. 4 is a view showing a concept of processing for obtaining a correction amount concerning a slice that is not a target of pre-scan.

It is to be noted that the pre-scan slices are not restricted to the first to Nth slices in the main scan-slices and they may be arbitrary slices. Further, three or more slices in the main scan slices may be determined as the pre-scan slices. FIG. 4 is a view showing a state of linear interpolation when slices at both ends and an intermediate slice in the main scan slices are determined as the pre-scan slices. In this case, the pre-scan time is reduced to 3/N as compared with an example where the N main scan slices are all subjected to the pre-scan, and the pre-scan time becomes longer than that in an example where the number of pre-scan slices is two. However, an accuracy of linear interpolation is improved, and a correction accuracy for the main scan slices that are not the pre-scan slices is enhanced.

In the pre-scan, some of spin echoes included in the spin echo train for one shot alone may be collected without collecting all data concerning target slices. For example, when the number of the spin echoes included in the spin echo train for one short is 20, approximately three in these spin echoes may be collected.

Second Embodiment

In a second embodiment, a main controller 10g serves as a unit that realizes the following several functions besides a unit that realizes functions generally provided in an MRI apparatus. One of the functions is controlling a gradient power supply 3, a transmitter 7, a receiver 8, a hybrid circuit 9, a data collection unit 10b, and others in such a manner that pre-scan concerning a plurality of pre-scan slices determined as some of main scan slices is performed with a smaller number of coverages than that in main scan. One of the functions is calculating a correction amount concerning each of the main scan slices determined as the pre-scan slices based on a pre-scan result of each slice. One of the functions is estimating a correction amount in relation to each slice other than the pre-scan slices in the main scan slices. One of the functions is controlling the gradient power supply 3, the transmitter 7, the receiver 8, the hybrid circuit 9, the data collection unit 10b, and others in such a manner that each of the main scan slices is scanned in a multi-slice mode involving correction with each correction amount calculated or estimated as explained above.

An operation of an MRI apparatus 100 in the second embodiment will now be explained.

In the second embodiment, the main scan is executed in the multi-slice mode. In the multi-slice mode, N/P slices in N main scan slices in one slab are scanned per repetition time TR with P coverages. Further, in the pre-scan, a slice gap is multiplied by P, and scan is performed with one coverage alone.

Figure 5:
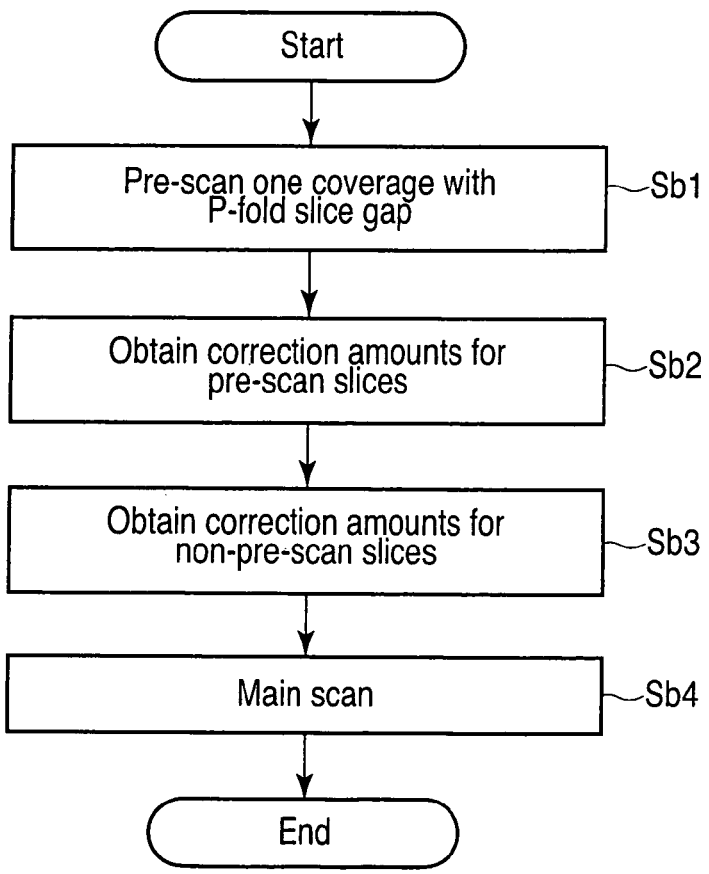
FIG. 5 is a flowchart showing an example of a processing procedure of the main controller in FIG. 1 according to the second embodiment.

FIG. 5 is a flowchart showing an example of a processing procedure of the main controller 10g in the second embodiment.

At step Sb1, the main controller 10g multiplies a slice gap by P with respect to the main scan, and controls the gradient power supply 3, the transmitter 7, the receiver 8, the hybrid circuit 9, and the data collection unit 10b to pre-scan one slab with one coverage. Therefore, the number of the pre-scan slices is N/P.

At step Sb2, the main controller 10g obtains each of correction amounts concerning the main scan slices determined as the pre-scan slices based on data collected in relation to each slice by the pre-scan. It is to be noted that a known technique can be used for a calculation of the correction amounts based on the data collected by the pre-scan.

At step Sb3, the main controller 10b obtains a correction amount for each of the slices that are not pre-scan targets in the main scan slices based on each correction amount acquired in relation to the main scan slices as the pre-scan slices. This can be executed like the first embodiment.

At step Sb4, the main controller 10g controls the gradient power supply 3, the transmitter 7, the receiver 8, the hybrid circuit 9, and the data collection unit 10b to execute the main scan. At this time, a 180-degree pulse obtained by correcting a phase based on each correction amount acquired at step Sb2 is used in relation to the main scan slices determined as the pre-scan slices, and a 180-degree pulse obtained by correcting a phase based on each correction amount acquired at step Sb3 is used in regard to the main scan slices that are not the pre-scan slices.

Thus, according to this embodiment, a pre-scan time can be shortened to 1/P as compared with a case where the N main scan slices are all subjected to the pre-scan.

Third Embodiment

In a third embodiment, a main controller log serves as a unit that realizes the following several functions besides a unit that realizes functions generally provided in an MRI apparatus. One of the functions is controlling a gradient power supply 3, a transmitter 7, a receiver 8, a hybrid circuit 9, a data collection unit 10b, and others in such a manner that pre-scan is executed in regard to a plurality of blades (which will be referred to as pre-scan blades hereinafter) determined as some of a plurality of blades (which will be referred to as main scan blades) as main scan targets. One of the functions is calculating a correction amount for each of the main scan blades determined as the pre-scan blades based on a pre-scan result of each blade. One of the functions is estimating a correction amount for each blade other than the pre-scan blades in the main scan blades based on each of the plurality of calculated correction amounts. One of the functions is controlling the gradient power supply 3, the transmitter 7, the receiver 8, the hybrid circuit 9, the data collection unit 10b, and others in such a manner that each of the main scan blades is scanned based on a blade rotation mode involving correction with each correction amount calculated or estimated in regard to each blade as explained above.

An operation of the MRI apparatus 100 in the third embodiment will now be explained.

In the third embodiment, the main scan is executed based on the blade rotation mode. In the blade rotation mode, a plurality of blades concerning one slice are collected one by one per repetition time TR. The blade includes a plurality of k-space trajectory parallel to each other. The plurality of blades are different from each other in inclination in the k-space.

FIG. 6 is a flowchart showing an example of a processing procedure of the main controller 10g in the third embodiment.

At step Sc1, the main controller 10g controls the gradient power supply 3, the transmitter 7, the receiver 8, the hybrid circuit 9, and the data collection unit 10b to collect respective pieces of data of 0- and 90-degree blades alone one by one per repetition time Tr. It is to be noted that a readout direction of the 0-degree blade matches the X-axis direction and a readout direction of the 90-degree blade matches the Y-axis direction as shown in FIG. 7. As a result, the pre-scan targeting the 0- and 90-degree blades alone in the main scan blades is executed.

At step Sc2, the main controller 10g obtains a correction amount for each of the 0- and 90-degree main scan blades based on the data collected by the pre-scan. Specifically, for example, a correction amount for a readout gradient magnetic field can be acquired from a difference in first order phase between a first echo and a second echo. A correction amount for the 0-degree main scan blade will be represented as $\Delta Gx$ and a correction amount for the 90-degree main scan blade will be represented as $\Delta Gy$ hereinafter.

At step Sc3, the main controller 10g acquires a correction amount for each main scan blade that is not the pre-scan target based on the correction amounts $\Delta Gx$ and $\Delta Gy$. For example, a correction amount for such a blade having an angle $\theta$ as shown in FIG. 7 can be represented by using a correction amount along the X-axis direction obtained from the following Expression (2) and a correction amount along the Y-axis direction obtained by Expression (3).

$$\Delta Gx \times \cos(\theta) \quad (2)$$

$$\Delta Gy \times \sin(\theta) \quad (3)$$

At step Sc4, the main controller 10g controls the gradient power supply 3, the transmitter 7, the receiver 8, the hybrid circuit 9, and the data collection unit 10b to execute the main scan. At this time, a gradient magnetic field corrected based on each correction amount obtained at step Sc2 is used in the main scan concerning 0- and 90-degree slices, and a gradient magnetic field corrected based on each correction amount obtained at step Sc3 is used in the main scan concerning blades having other angles.

Thus, according to this embodiment, a pre-scan time can be reduced to 2/Q as compared with a case where Q blades are all subjected to the pre-scan.

It is to be noted that the blades as the pre-scan targets are not restricted to the 0- and 90-degree blades, and other arbitrary blades in the main scan blades can be determined as the pre-scan targets. Assuming that angles of two blades as the pre-scan targets are represented as $\theta 1$ and $\theta 2$ and gradient magnetic field correction amounts obtained based on the pre-scan concerning these two blades are represented as G1 and G2, the correction amounts $\Delta Gx$ and $\Delta Gy$ can be obtained by solving the following simultaneous equations.

$$\Delta Gx \times |\cos(\theta 1)| + Gy \times |\sin(\theta 1)| = G1$$

$$\Delta Gx \times |\cos(\theta 2)| + Gy \times |\sin(\theta 2)| = G2$$

That is, correction amounts for the blade having the angle $\theta$ are $\Delta Gx \times \cos(\theta)$ along in the X-axis direction and $\Delta Gy \times \sin(\theta)$ along the Y-axis direction.

On the other hand, in regard to correction for a 180-degree pulse, when a phase shift caused due to a slice gradient magnetic field is dominant, an average of the correction amounts obtained from the above-explained two blades can be used to be common to all blades. However, when an effect of a readout gradient magnetic field cannot be ignored, blades having three y arbitrary different angles (angles $\theta 1$, $\theta 2$, and $\theta 3$) are determined as pre-scan targets. Further, when correction amounts obtained based on the pre-scan concerning these three blades are represented as A1, A2, and A3, correction amounts Ax, Ay, and Az for the respective X, Y, and Z axes can be obtained by solving the following simultaneous equations.

$$Az + Ax \times \cos(\theta 1) + Ay \times \sin(\theta 1) = A1$$

$$Az + Ax \times \cos(\theta 2) + Ay \times \sin(\theta 2) = A2$$

$$Az + Ax \times \cos(\theta 3) + Ay \times \sin(\theta 3) = A3$$

That is, a correction amount for the blade having the angle $\theta$ is $Az + Ax \times \cos(\theta) + Ay \times \sin(\theta)$.

The blades used as the pre-scan targets may be three or more. Where the main scan targets are 30 blades, it is thought to perform the pre-scan, using 3 to 5 blades.

More specifically, where the number of blades used for the pre-scan is m ($m \geq 2$), the pre-scan is executed m times at each of different blade angles $\theta i$. The gradient magnetic field correction amount Gi obtained by performing a pre-scan with respect to a slice having blade angle $\theta i$, is expressed by the following formula:

$$\Delta Gx \times |\cos(\theta i)| + \Delta Gy \times |\sin c(\theta i)| = Gi$$

Where m=2, the two simultaneous equations obtained by substituting 1 and 2 for i are solved, thereby uniquely determining values of $\Delta Gx$ and $\Delta Gy$.

Where m>2, optimal values of $\Delta Gx$ and $\Delta Gy$ are determined by a known interpolation method.

The gradient magnetic field correction amount Gi for the main scan at blade angle $\theta i$ can be obtained based on the formula set forth below, using the values of $\Delta Gx$ and $\Delta Gy$ determined as above.

$$Gj = \Delta Gx \times |\cos(\theta j)| + \Delta Gy \times |\sin c(\theta j)|$$

The 180-degree pulse correction amount Ai for the main scan at blade angle $\theta i$ can be obtained based on the formula set forth below.

$$Aj = Az + Ax \times |\cos(\theta j)| + Ay \times |\sin(\theta j)|$$

When the number of blades used as the pre-scan targets is increased, a longer time is required for the pre-scan, but the correction amounts for the blades that are not used as pre-scan targets can be determined with higher accuracy.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging apparatus comprising:
   a collection unit which collects a magnetic resonance signal concerning a subject in a fast spin echo sequence or a fast asymmetric spin echo sequence;
   a pre-scan control unit which controls the collection unit in such a manner that pre-scan is executed in regard to a plurality of slices determined as some of a plurality of slices that are main scan targets;
   a calculation unit which calculates at least one of correction amounts for a gradient magnetic field in a readout direction and a phase of a radio-frequency pulse based on data concerning a plurality of slices obtained by the pre-scan;
   an estimation unit which estimates a correction amount concerning each slice other the plurality of pre-scanned slices in the plurality of slices that are the main scan targets based on a plurality of correction amounts calculated by the calculation unit; and a main scan control unit which controls the collection unit in such a manner that each of the plurality of slices as the main scan targets is scanned while involving correction of each slice that is the pre-scan target with the correction amount thereof calculated by the calculation unit and while involving correction of each slice that is not the pre-scan target with the correction amount thereof estimated by the estimation unit.

2. The magnetic resonance imaging apparatus according to claim 1, wherein the main scan control unit controls the collection unit in such a manner that the main scan is executed in a sequential mode where a plurality of slices in one slab are scanned one by one per repetition time, and the pre-scan control unit controls the collection unit in such a manner that the plurality of slices as the pre-scan targets are scanned one by one per repetition time.

3. The magnetic resonance imaging apparatus according to claim 2, wherein the pre-scan control unit collects data concerning some of a plurality of spin echoes included in a spin echo train corresponding to one shot alone in regard to each of the plurality of slices as the pre-scan targets.

4. The magnetic resonance imaging apparatus according to claim 1, wherein the main scan control unit controls the collection unit in such a manner that the main scan is executed in a multi-slice mode where more than one in a plurality of slices in one slab are scanned per repetition time with a plurality of coverages, and the pre-scan control unit controls the collection unit in such a manner that a slice gap is increased to be larger than that in the main scan and the number of coverages is reduced to be smaller than those in the main scan to execute the pre-scan.

5. The apparatus according to claim 4, wherein the pre-scan control unit controls the collection unit in such a manner that the pre-scan is executed with a slice gap in the pre-scan that is m-fold of the slice gap to be used in the main scan and with one pre-scan coverage, where m is the number of coverages to be used in the main scan.

6. The apparatus according to claim 1, wherein the estimation unit estimates a correction amount by linear interpolation based on the plurality of correction amounts calculated by the calculation unit.

7. A magnetic resonance imaging apparatus comprising:

a collection unit which collects a magnetic resonance signal concerning a subject in accordance with each of blades including a plurality of k-space trajectory parallel to each other and having different inclinations in the k-space in one of a fast spin echo sequence and a fast asymmetric spin echo sequence;

pre-scan control unit which controls the collection unit in such a manner that a plurality of blades determined as some of a plurality of blades that are main scan targets are pre-scanned;

a calculation unit which calculates a calculation amount for at least one of a gradient magnetic field in a readout direction and a phase of a radio-frequency pulse based on data concerning a plurality of blades obtained by the pre-scan;

an estimation unit which estimates a correction amount in regard to each blade other than the pre-scan target blades in the plurality of main scan target blades based on a plurality of correction amounts calculated by the calculation unit; and a main scan control unit which controls the collection unit in such a manner that each of the plurality of blades as the main scan targets is scanned while involving correction for each of the blades that are the pre-scan targets with a correction amount thereof calculated by the calculation unit or while involving correction for each of the blades that are not the pre-scan targets with a correction amount thereof estimated by the estimation unit.

8. A magnetic resonance imaging method in a magnetic resonance imaging apparatus including a collection unit which collects a magnetic resonance signal concerning a subject in a fast spin echo sequence or a fast asymmetric spin echo sequence, comprising:

controlling the collection unit in such a manner that a plurality of slices determined as some of a plurality of slices that are main scan targets are pre-scanned;

calculating a correction amount for at least one of a gradient magnetic field in a readout direction or a phase of a radio-frequency pulse based on data concerning a plurality of slices obtained by the pre-scan;

estimating a correction amount concerning each slice other than the plurality of pre-scanned slices in the plurality of slices that are the main scan targets based on the plurality of calculated correction amounts; and controlling the collection unit in such a manner that each of the plurality of slices that are the main scan targets is scanned while involving correction for each of the slices as the pre-scan targets with the calculated correction amount thereof or while involving correction of each of the slices that are not the pre-scan targets with the estimated correction amount thereof.

9. A magnetic resonance imaging method in a magnetic resonance imaging apparatus including a collection unit which collects a magnetic resonance signal concerning a subject in accordance with each of blades including a plurality of k-space trajectory parallel to each other and having different inclinations in the k-space in one of a fast spin echo sequence or a fast asymmetric spin echo sequence, comprising:

controlling the collection unit in such a manner that a plurality of blades determined as some of a plurality of blades that are main scan targets are pre-scanned;

calculating a correction amount for at least one of a gradient magnetic field in a readout direction and a phase of a radio-frequency pulse based on data concerning a plurality of blades obtained by the pre-scan;

estimating a correction amount of each blade other than the pre-scan target blades in the plurality of main scan target blades based on the plurality of calculated correction amounts; and controlling the collection unit in such a manner that each of the plurality of blades that are the main scan targets is scanned while involving correction of each of the blades that are the pre-scan targets with the calculated correction amount thereof or while involving correction of each of the blades that are not the pre-scan targets with the estimated correction amount thereof.

* * * * *